(12) United States Patent
Brookings et al.

US008487101B2

(10) Patent No.: US 8,487,101 B2
(45) Date of Patent: Jul. 16, 2013

(54) THIENO-PYRIDINE DERIVATIVES AS MEK INHIBITORS

(75) Inventors: Daniel Christopher Brookings, Slough (GB); Martin Clive Hutchings, Slough (GB); Barry John Langham, Slough (GB)

(73) Assignee: UCB Pharma S.A., Brussels (BE)

( * ) Notice: Subject to any disclaimer, the term of this patent is extended or adjusted under 35 U.S.C. 154(b) by 233 days.

(21) Appl. No.: 12/839,752

(22) Filed: Jul. 20, 2010

(65) Prior Publication Data

US 2011/0021558 A1    Jan. 27, 2011

Related U.S. Application Data

(63) Continuation of application No. PCT/GB2009/00144, filed on Jan. 20, 2009.

(30) Foreign Application Priority Data

Jan. 21, 2008    (GB) .................................. 0801082.9
Jul. 9, 2008    (GB) .................................. 0812563.5

(51) Int. Cl.
*C07D 495/04*    (2006.01)
(52) U.S. Cl.
USPC ......................................... 546/114; 514/301
(58) Field of Classification Search
USPC .......................................... 546/114; 514/301
See application file for complete search history.

(56) References Cited

U.S. PATENT DOCUMENTS

| | | |
|---|---|---|
| 2003/0220365 A1 | 11/2003 | Stewart |
| 2004/0138251 A1 | 7/2004 | Boschelli |
| 2005/0049276 A1 | 3/2005 | Kaufman |
| 2005/0227959 A1 | 10/2005 | Yoshida |
| 2007/0049603 A1 | 3/2007 | Miknis |
| 2009/0149437 A1 | 6/2009 | Hutchings |
| 2009/0264411 A1 | 10/2009 | Laing |
| 2010/0179124 A1 | 7/2010 | Johnson |
| 2011/0172191 A1 | 7/2011 | Johnson |

FOREIGN PATENT DOCUMENTS

| | | |
|---|---|---|
| WO | WO 02/06213 | 1/2002 |
| WO | WO 03/077855 | 9/2003 |
| WO | WO 03/077914 | 9/2003 |
| WO | WO 2004/000846 | 12/2003 |
| WO | WO 2004/113347 | 12/2004 |
| WO | WO 2004/113348 | 12/2004 |
| WO | WO 2005/009975 | 2/2005 |
| WO | WO 2005/023251 | 3/2005 |
| WO | WO 2005/023759 | 3/2005 |
| WO | WO 2005/023818 | 3/2005 |
| WO | WO 2005/051300 | 6/2005 |
| WO | WO 2005/051906 | 6/2005 |
| WO | WO 2007/044515 | 4/2007 |
| WO | WO 2007/088345 | 8/2007 |
| WO | WO 2007/120101 | 10/2007 |
| WO | WO 2008/020206 | 2/2008 |
| WO | WO 2009013462 A1 * | 1/2009 |

OTHER PUBLICATIONS

Roberts et. al. "Targeting the Raf-MEK-ERK mitogen-activated protein kinase cascade for the treatment of cancer." Oncogene (2007) 26, 3291-3310.*
Simone, Oncology: Introduction, Cecil Textbook of Medicine, 20th Edition, 1996 vol. 1, pp. 1004-1010.*
Trisha Gura "Cancer Models: Systems for Identifying New Drugs Are Often Faulty" Science Nov. 7, 1997: vol. 278. No. 5340, pp. 1041-1042.*
Bremner, D.H. et al,: "The Synthesis of Thienopyridines from *ortho*-Halogenated Pyridine Derivatives; Part 2" Synthesis, 1997, pp. 949-952.
Bremner, D.H. et al.: "The Synthesis of Thienopyridines from *ortho*-Halogenated Pyridine Derivatives; Part 3" Synthesis, 1998, pp. 1095-1097.
Byrn et al., "Solid-State Chemistry of Drugs," $2^{nd}$ Ed., SSCI, Inc., West Lafayette, IN, Ch. 11, 1991, pp. 233-247.
Erian, Ayman Wahba et al: "An Easy Direct Conversion of Pyridine- and Pyrimidine-Thiones into Multi-Fused Heterocyclic Compounds" Bulletin of the Chemical Society of Japan, 71(10), 1998, pp. 2387-2391.
Hamdouchi et. al. "Structure-based design of a new class of highly selective aminoimidazo [1, 2-a] pyridine-based inhibitors of cyclin dependent kinases" Bioorganic & Medical Chemistry Letters 15, 2005, pp. 1943-1947.
Klemm L. H. et al., "Chemistry of Thienopyridines. XVII. Direct Halogenation of Thieno [2,3-b] pyridine (1)," *Journal of Heterocyclic Chemistry*, 1974, pp. 205-209.
Wermuth, Camille G. "Molecular Variation Based on Isosteric Replacements" in Chapter 13, The Practice of Medicinal Chemistry, Academic, 1996, pp. 203-237.
West, Anthon R., Solid State Chemistry and its Applications, Wiley, New York, 1988, pp. 358 & 365.
Written Opinion of the International Searching Authority published Jul. 31, 2008 for PCT/GB2007/000310 filed Jan. 30, 2007.
Written Opinion of the International Searching Authority published Feb. 15, 2009 for PCT/GB2007/003114 filed Aug. 15, 2007.
Written Opinion of the International Searching Authority published Jan. 23, 2010 for PCT/GB2008/002430 filed Jul. 16, 2008.
Written Opinion of the International Searching Authority published Jul. 21, 2010 for PCT/GB2009/000144 filed Jan. 20, 2009.
Written Opinion of the International Searching Authority published Dec. 19, 2010 for PCT/GB2009/001504 filed Jun. 12, 2009.
International Search Report published Aug. 9, 2007 for PCT/GB2007/000310 filed Jan. 30, 2007.
International Search Report published Apr. 24, 2008 for PCT/GB2007/003114 filed Aug. 15, 2007.

(Continued)

*Primary Examiner* — David K O Dell
(74) *Attorney, Agent, or Firm* — Walter C. Frank; Feldman Gale, P.A.

(57) ABSTRACT

A series of thieno[2,3-b]pyridine derivatives which are substituted in the 2-position by a substituted anilino moiety, being selective inhibitors of human MEK (MAPKK) enzymes, are accordingly of benefit in medicine, for example in the treatment of inflammatory, autoimmune, cardiovascular, proliferative (including oncological) and nociceptive conditions.

18 Claims, No Drawings

OTHER PUBLICATIONS

International Search Report published Jan. 29, 2009 for PCT/GB2008/002430 filed Jul. 16, 2008.

International Search Report published Jul. 30, 2009 for PCT/GB2009/000144 filed Jan. 20, 2009.

International Search Report published Dec. 23, 2009 for PCT/GB2009/001504 filed Jun. 12, 2009.

International Preliminary Report on Patentability published Aug. 5, 2008 for PCT/GB2007/000310 filed Jan. 30, 2007.

International Preliminary Report on Patentability published Feb. 17, 2009 for PCT/GB2007/003114 filed Aug. 15, 2007.

International Preliminary Report on Patentability published Jan. 26, 2010 PCT/GB2008/002430 filed Jul. 16, 2008.

International Preliminary Report on Patentability published Jul. 27, 2010 for PCT/GB2009/000144 filed Jan. 20, 2009.

International Preliminary Report on Patentability published Dec. 21, 2010 for PCT/GB2009/001504 filed Jun. 12, 2009.

* cited by examiner

THIENO-PYRIDINE DERIVATIVES AS MEK INHIBITORS

CROSS-REFERENCE TO RELATED APPLICATIONS

The present application is a continuation of International Application No. PCT/GB2009/000144, filed Jan. 20, 2009, which claims priority under 119(a-d) to Great Britain Application No. GB 0801082.9, filed Jan. 21, 2008 and to Great Britain Application No. GB 0812563.5, filed Jul. 9, 2008, each of which is hereby incorporated herein by reference in their entireties.

The present invention relates to a class of thieno-pyridine derivatives and to their use in therapy. More particularly, the invention is concerned with thieno[2,3-b]pyridine derivatives which are substituted in the 2-position by a substituted anilino moiety. These compounds are selective inhibitors of MEK (MAPKK) enzymes, and are accordingly of benefit as pharmaceutical agents, especially in the treatment of adverse inflammatory, autoimmune, cardiovascular, proliferative (including oncological) and nociceptive conditions.

MEK enzymes are implicated in a variety of physiological and pathological functions that are believed to be operative in a range of human diseases. These functions are summarised in paragraphs [0004] and [0005] of US 2005/0049276 A1.

The compounds of use in the present invention, being potent and selective MEK inhibitors, are therefore beneficial in the treatment and/or prevention of various human ailments. These include autoimmune and inflammatory disorders such as rheumatoid arthritis, osteoarthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); proliferative disorders such as restenosis, and oncological conditions including leukaemia, glioblastoma, lymphoma, melanoma, and human cancers of the liver, bone, skin, brain, pancreas, lung, breast, stomach, colon, rectum, prostate, ovary and cervix; and pain and nociceptive disorders, including chronic pain and neuropathic pain.

In addition, the compounds of use in the present invention may be beneficial as pharmacological standards for use in the development of new biological tests and in the search for new pharmacological agents. Thus, the compounds of use in this invention may be useful as radioligands in assays for detecting compounds capable of binding to human MEK enzymes.

MEK inhibitors based on a fused bicyclic aromatic ring system attached to a substituted anilino moiety are known from the art, such as from WO 2007/088345.

Nowhere in the prior art, however, is there the precise disclosure of a class of thieno[2,3-b]pyridine derivatives, attached at the 2-position to a substituted anilino moiety, which are substituted in the 3-position by a cyclic hydroxamate moiety. It has now been found that such compounds are particularly valuable as selective inhibitors of MEK enzymes.

The compounds of the present invention are potent and selective MEK inhibitors having a binding affinity ($IC_{50}$) for the human MEK1 and/or MEK2 enzyme of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human MEK1 and/or MEK2 enzyme relative to other human kinases.

The compounds of the present invention possess high potency, and interesting pharmacokinetic properties owing to their improved solubility and clearance.

The present invention provides a compound of formula (I), or a pharmaceutically acceptable salt, solvate or N-oxide thereof:

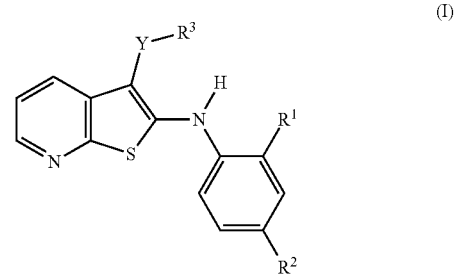

(I)

wherein
Y represents a linkage of formula C(O) or S(O)$_2$;
$R^1$ represents hydrogen, halogen, cyano, nitro, $C_{1-6}$ alkyl, trifluoromethyl, $C_{1-6}$ alkoxy, trifluoromethoxy, $C_{1-6}$ alkylthio, $C_{1-6}$ alkylsulphinyl or $C_{1-6}$ alkylsulphonyl;
$R^2$ represents halogen, nitro, cyano, $C_{1-6}$ alkyl, $C_{2-6}$ alkynyl, hydroxy($C_{1-6}$)alkyl or formyl; and
$R^3$ represents a group of formula (a), (b), (c), (d) or (e):

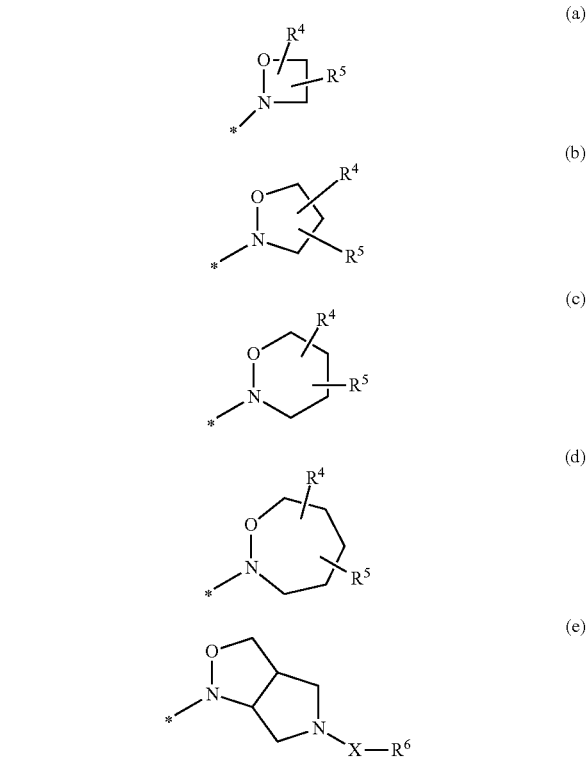

wherein the asterisk (*) represents the point of attachment to the remainder of the molecule;
$R^4$ and $R^5$ independently represent hydrogen, $C_{1-6}$ alkyl, $C_{1-6}$ alkoxy, $C_{1-6}$ alkylamino($C_{1-6}$)alkoxy, $C_{1-6}$ alkoxy($C_{1-6}$)

alkyl, C_{1-6} alkylthio, C_{1-6} alkylsulphonyl, hydroxy, hydroxy(C_{1-6})alkyl, amino(C_{1-6})alkyl, nitro(C_{1-6})alkyl, cyano, trifluoromethyl, C_{2-6} alkylcarbonyl, carboxy, C_{2-6} alkoxycarbonyl, azido, amino, C_{1-6} alkylamino, di(C_{1-6})alkylamino, bis[hydroxy(C_{1-6})alkyl]amino, C_{1-6} alkylamino(C_{1-6}) lkylamino, arylamino, heteroarylamino, C_{2-6} alkylcarbonylamino, C_{2-6} alkoxycarbonylamino, [(C_{2-6})alkoxycarbonyl][(C_{1-6})alkyl]amino, bis[C_{2-6})alkoxycarbonyl(C_{1-6})alkyl]amino, C_{2-6} alkoxycarbonylamino(C_{1-6})alkyl or aminocarbonyl;

X represents a covalent bond, or a linkage of formula C(O), S(O)_2, C(O)O or C(O)N(R^7);

R^6 represents hydrogen or trifluoromethyl; or C_{1-6} alkyl, C_{3-7} cycloalkyl, C_{3-7} cycloalkyl(C_{1-6})alkyl, aryl, aryl(C_{1-6}) alkyl, C_{3-7} heterocycloalkyl, C_{3-7} heterocycloalkyl-(C_{1-6}) alkyl, heteroaryl or heteroaryl(C_{1-6})alkyl, any of which groups may be optionally substituted by one or more substituents; and R^7 represents hydrogen or C_{1-6} alkyl.

Where a group in the compounds of formula (I) above is stated to be optionally substituted, this group may be unsubstituted, or substituted by one or more substituents. Typically, such a group will be unsubstituted, or substituted by one or two substituents. Suitably, such a group will be unsubstituted or monosubstituted.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched C_{1-6} alkyl groups, for example C_{1-4} alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl and 2,2-dimethylpropyl. Derived expressions such as "C_{1-6} alkoxy", "C_{1-6} alkylthio", "C_{1-6} alkylsulphonyl" and "C_{1-6} alkylamino" are to be construed accordingly.

Specific C_{3-7} cycloalkyl groups are cyclopropyl, cyclobutyl, cyclopentyl, cyclohexyl and cycloheptyl.

Suitable aryl groups include phenyl and naphthyl, preferably phenyl.

Suitable aryl(C_{1-6})alkyl groups include benzyl, phenylethyl, phenylpropyl and naphthylmethyl.

Suitable heterocycloalkyl groups, which may comprise benzo-fused analogues thereof, include azetidinyl, tetrahydrofuranyl, dioxolanyl, pyrrolidinyl, indolinyl, imidazolidinyl, tetrahydropyranyl, piperidinyl, 1,2,3,4-tetrahydroquinolinyl, 1,2,3,4-tetrahydroisoquinolinyl, piperazinyl, morpholinyl and thiomorpholinyl.

Suitable heteroaryl groups include furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, pyridinyl, quinolinyl, isoquinolinyl, pyridazinyl, pyrimidinyl, pyrazinyl and triazinyl groups.

The term "halogen" as used herein is intended to include fluorine, chlorine, bromine and iodine atoms.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto (CH_2C=O)↔enol (CH=CHOH) tautomers or amide (NHC=O)↔hydroxyimine (N=COH) tautomers. Formula (I) and the formulae depicted hereinafter are intended to represent all individual tautomers and all possible mixtures thereof, unless stated or shown otherwise.

Suitable values of R^1 include hydrogen, halogen and C_{1-6} alkyl. In one embodiment, R^1 represents hydrogen. In a particular embodiment, R^1 represents halogen, especially fluoro or chloro. In another embodiment, R^1 represents C_{1-6} alkyl, especially methyl.

Suitably, R^1 represents halogen. In a particular embodiment, R^1 is fluoro. In another embodiment, R^1 is chloro.

Suitably, R^2 represents halogen, nitro, cyano, C_{2-6} alkynyl, hydroxy(C_{1-6})alkyl or formyl. Typically, R^2 represents halogen, nitro, hydroxy(C_{1-6})alkyl or formyl.

In one embodiment, R^2 represents halogen, especially bromo or iodo, particularly iodo. In another embodiment, R^2 represents nitro. In another embodiment, R^2 represents cyano. In another embodiment, R^2 represents C_{1-6} alkyl, especially methyl. In another embodiment, R^2 represents C_{2-6} alkynyl, especially ethynyl. In a further embodiment, R^2 represents hydroxy(C_{1-6})alkyl, especially hydroxymethyl. In an additional embodiment, R^2 represents formyl.

Specific sub-classes of compounds in accordance with the present invention are represented by the compounds of formula (IA), (IB), (IC), (ID) and (IE):

(IA)

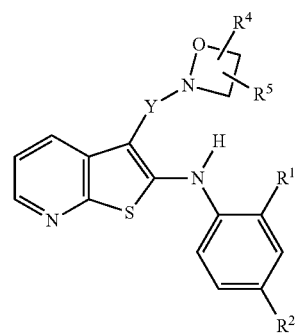

-continued

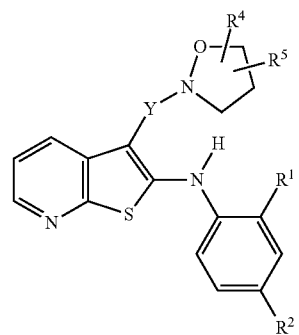
(IB)

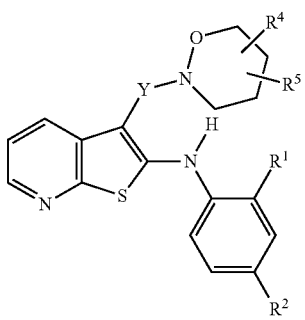
(IC)

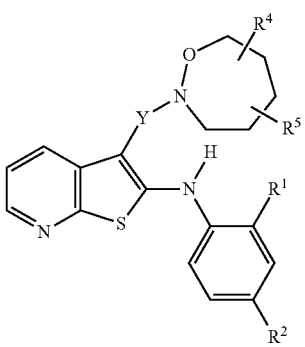
(ID)

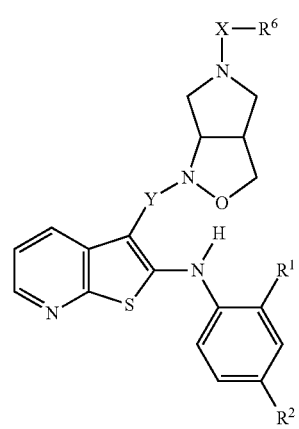
(IE)

wherein Y, R¹, R², R⁴, R⁵, X and R⁶ are as defined above.

One particular sub-class of compounds in accordance with the present invention is represented by the compounds of formula (IB) as depicted above. Another particular sub-class of compounds in accordance with the present invention is represented by the compounds of formula (IE) as depicted above.

The ring fusion between the isoxazolidine and pyrrolidine rings in the compounds of formula (IE) as depicted above is suitably in the cis configuration, giving rise to a particular sub-class of compounds of formula (IE-1):

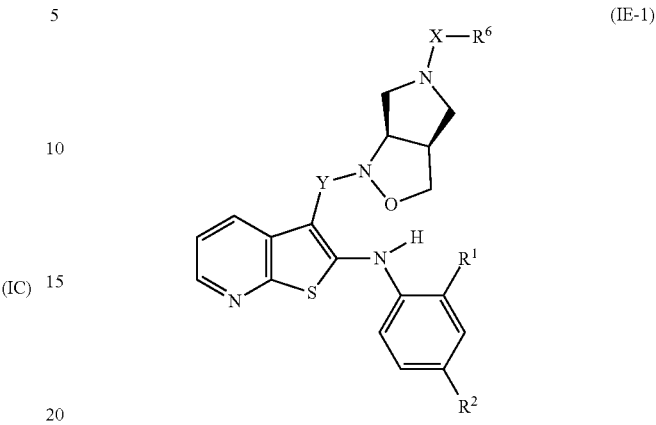
(IE-1)

wherein Y, R¹, R², X and R⁶ are as defined above.

In one embodiment, Y represents a linkage of formula C(O), whereby the present invention provides a compound of formula (IF), or a pharmaceutically acceptable salt, solvate or N-oxide thereof:

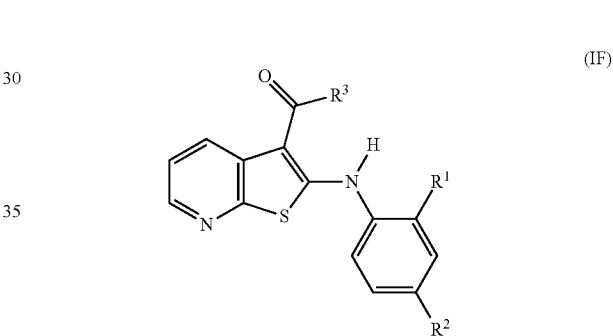
(IF)

wherein R¹, R² and R³ are as defined above.

In another embodiment, Y represents a linkage of formula S(O)₂, whereby the present invention provides a compound of formula (IG), or a pharmaceutically acceptable salt, solvate or N-oxide thereof:

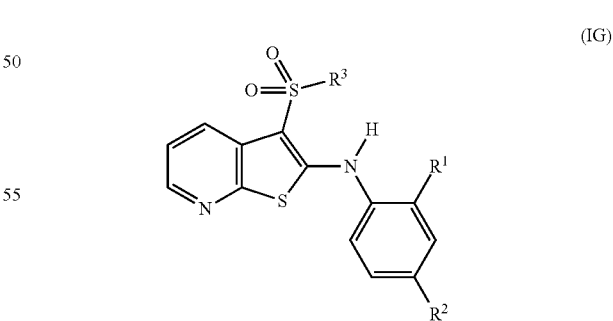
(IG)

wherein R¹, R² and R³ are as defined above.

Typically, R³ represents a group of formula (b) or (e) as depicted above.

In one embodiment, R³ represents a group of formula (a) as depicted above. In another embodiment, R³ represents a group of formula (b) as depicted above. In a further embodiment, $R^3$ represents a group of formula (c) as depicted above. In a still further embodiment, $R^3$ represents a group of formula (d) as depicted above. In an additional embodiment, $R^3$ represents a group of formula (e) as depicted above.

Suitably, $R^3$ represents a group of formula (b) as depicted above.

Suitably, $R^4$ and $R^5$ independently represent hydrogen, $C_{1-6}$ alkyl, $C_{1-6}$ alkoxy, $C_{1-6}$ alkylamino($C_{1-6}$)alkoxy, $C_{1-6}$ alkoxy($C_{1-6}$)alkyl, $C_{1-6}$ alkylthio, $C_{1-6}$ alkylsulphonyl, hydroxy, hydroxy($C_{1-6}$)alkyl, amino($C_{1-6}$)alkyl, nitro($C_{1-6}$)alkyl, cyano, trifluoromethyl, $C_{2-6}$ alkylcarbonyl, carboxy, $C_{2-6}$ alkoxycarbonyl, amino, $C_{1-6}$ alkylamino, di($C_{1-6}$)alkylamino, bis[hydroxy($C_{1-6}$)alkyl]amino, $C_{1-6}$ alkylamino($C_{1-6}$)alkylamino, arylamino, heteroarylamino, $C_{2-6}$ alkylcarbonylamino, $C_{2-6}$ alkoxycarbonylamino, [($C_{2-6}$)alkoxycarbonyl][($C_{1-6}$)alkyl]amino, bis[($C_{2-6}$)alkoxycarbonyl($C_{1-6}$)alkyl]amino, $C_{2-6}$ alkoxycarbonylamino($C_{1-6}$)alkyl or aminocarbonyl.

Typical values of $R^4$ and/or $R^5$ include hydrogen, $C_{1-6}$ alkyl, $C_{1-6}$ alkoxy($C_{1-6}$)-alkyl, hydroxy, hydroxy($C_{1-6}$)alkyl, amino($C_{1-6}$)alkyl, $C_{2-6}$ alkoxycarbonyl, amino, $C_{1-6}$ alkylamino, di($C_{1-6}$)alkylamino, $C_{2-6}$ alkylcarbonylamino, $C_{2-6}$ alkoxycarbonylamino, bis[($C_{2-6}$)alkoxycarbonyl($C_{1-6}$)alkyl]amino, $C_{2-6}$ alkoxycarbonylamino($C_{1-6}$)alkyl and aminocarbonyl.

Particular values of $R^4$ and/or $R^5$ include hydrogen, methyl, ethyl, isopropyl, methoxy, isopropoxy, methylaminoethoxy, methoxymethyl, methylthio, ethylthio, methylsulphonyl, hydroxy, hydroxymethyl, hydroxyethyl, aminomethyl, nitromethyl, cyano, trifluoromethyl, acetyl, carboxy, methoxycarbonyl, ethoxycarbonyl, tert-butoxycarbonyl, amino, methylamino, ethylamino, dimethylamino, bis[hydroxyethyl]amino, ethylaminoethylamino, phenylamino, pyridinylamino, acetylamino, tert-butoxycarbonylamino, (tert-butoxycarbonyl)(methyl)amino, bis(ethoxycarbonylmethyl)amino, tert-butoxycarbonylaminomethyl and aminocarbonyl.

Selected values of $R^4$ and/or $R^5$ include hydrogen, $C_{1-6}$ alkyl, hydroxy, hydroxy($C_{1-6}$)alkyl, carboxy, $C_{2-6}$ alkoxycarbonyl, azido and amino.

Specific values of $R^4$ and/or $R^5$ include hydrogen, methyl, hydroxy, hydroxymethyl, carboxy, methoxycarbonyl, azido and amino.

Selected values of $R^4$ include hydrogen, $C_{1-6}$ alkyl, hydroxy, hydroxy($C_{1-6}$)alkyl, carboxy, $C_{2-6}$ alkoxycarbonyl, azido and amino.

Specific values of $R^4$ include hydrogen, methyl, hydroxy, hydroxymethyl, carboxy, methoxycarbonyl, azido and amino.

Suitably, $R^4$ represents hydrogen, hydroxy or amino.

In one embodiment, $R^4$ represents hydrogen. In a particular embodiment, $R^4$ represents hydroxy. In another embodiment, $R^4$ represents amino. In a further embodiment, $R^4$ represents $C_{1-6}$ alkyl, especially methyl. In a further embodiment, $R^4$ represents hydroxy($C_{1-6}$)alkyl, especially hydroxymethyl. In a further embodiment, $R^4$ represents carboxy. In a further embodiment, $R^4$ represents $C_{2-6}$ alkoxycarbonyl, especially methoxycarbonyl. In a further embodiment, $R^4$ represents azido.

Selected values of $R^5$ include hydrogen, $C_{1-6}$ alkyl, hydroxy and amino. Particular values of $R^5$ include hydrogen and $C_{1-6}$ alkyl.

Suitably, $R^5$ represents hydrogen, hydroxy or amino.

In a favoured embodiment, $R^5$ represents hydrogen. In another embodiment, $R^5$ represents hydroxy. In a further embodiment, $R^5$ represents amino. In a still further embodiment, $R^5$ represents $C_{1-6}$ alkyl, especially methyl.

Suitably, X represents a covalent bond, or a linkage of formula C(O), S(O)$_2$ or C(O)N($R^7$), in which $R^7$ is as defined above.

Typically, X represents a covalent bond, or a linkage of formula C(O)O.

In a favoured embodiment, X represents a covalent bond. In another embodiment, X represents a linkage of formula C(O). In a further embodiment, X represents a linkage of formula S(O)$_2$. In a still further embodiment, X represents a linkage of formula C(O)O. In an additional embodiment, X represents a linkage of formula C(O)N($R^7$).

Suitably, $R^6$ represents hydrogen; or $C_{1-6}$ alkyl, $C_{3-7}$ cycloalkyl($C_{1-6}$)alkyl, aryl-($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Typically, $R^6$ represents hydrogen; or $C_{1-6}$ alkyl or aryl($C_{1-6}$)alkyl, either of which groups may be optionally substituted by one or more substituents.

Appositely, $R^6$ represents hydrogen or optionally substituted aryl($C_{1-6}$)alkyl.

Illustratively, $R^6$ represents hydrogen; or methyl, ethyl, propyl, butyl, pentyl, hexyl, cyclohexylmethyl, benzyl, phenylethyl, azetidinyl, tetrahydrofuryl, tetrahydrothienyl, pyrrolidinyl, piperidinyl, homopiperidinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylethyl, morpholinylpropyl, pyridinyl, indolylethyl, pyrazolylethyl, imidazolylmethyl, imidazolylethyl, benzimidazolylmethyl, triazolylethyl, pyridinylmethyl or pyridinylethyl, any of which groups may be optionally substituted by one or more substituents.

Examples of typical substituents on $R^6$ include halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl and di($C_{1-6}$)-alkylaminosulphonyl.

Examples of particular substituents on $R^6$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, acetylamino, methoxycarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl.

Typically, $R^6$ represents hydrogen, $C_{1-6}$ alkyl or aryl($C_{1-6}$)alkyl. Suitably, $R^6$ represents hydrogen or $C_{1-6}$ alkyl. Appositely, $R^6$ represents hydrogen or aryl($C_{1-6}$)alkyl. In one embodiment, $R^6$ represents hydrogen. In another embodiment, $R^6$ represents $C_{1-6}$ alkyl, especially methyl. In a further embodiment, $R^6$ represents aryl($C_{1-6}$)alkyl, especially benzyl.

In one embodiment, $R^7$ represents hydrogen. In another embodiment, $R^7$ represents $C_{1-6}$ alkyl, especially methyl.

One sub-class of compounds according to the invention is represented by the compounds of formula (IIA), and pharmaceutically acceptable salts, solvates and N-oxides thereof:

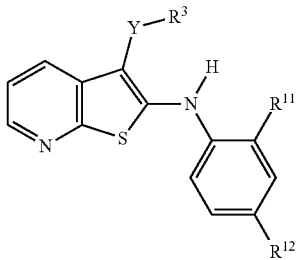

(IIA)

wherein
Y and $R^3$ are as defined above;
$R^{11}$ represents halogen; and
$R^{12}$ represents halogen, nitro, cyano, $C_{2-6}$ alkynyl, hydroxy ($C_{1-6}$)alkyl or formyl.

In one specific embodiment, $R^{11}$ is fluoro. In another specific embodiment, $R^{11}$ is chloro.

Typically, $R^{12}$ represents halogen, nitro, hydroxy($C_{1-6}$) alkyl or formyl.

In one embodiment, $R^{12}$ represents halogen, especially iodo. In another embodiment, $R^{12}$ represents nitro. In another embodiment, $R^{12}$ represents cyano. In another embodiment, $R^{12}$ represents $C_{2-6}$ alkynyl, especially ethynyl. In a further embodiment, $R^{12}$ represents hydroxy($C_{1-6}$)alkyl, especially hydroxymethyl. In an additional embodiment, $R^{12}$ represents formyl.

A particular sub-group of the compounds of formula (IIA) is represented by the compounds of formula (IIB), and pharmaceutically acceptable salts, solvates and N-oxides thereof:

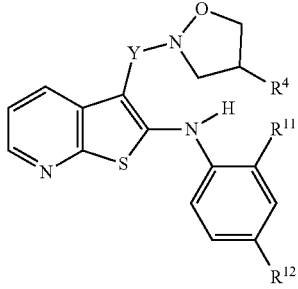

(IIB)

wherein
Y, $R^4$, $R^{11}$ and $R^{12}$ are as defined above.

Another sub-group of the compounds of formula (IIA) is represented by the compounds of formula (IIC), and pharmaceutically acceptable salts, solvates and N-oxides thereof:

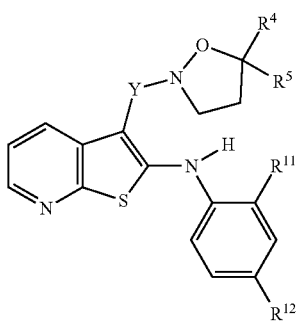

(IIC)

wherein
Y, $R^4$, $R^5$, $R^{11}$ and $R^{12}$ are as defined above.

A further sub-group of the compounds of formula (IIA) is represented by the compounds of formula (IID), and pharmaceutically acceptable salts, solvates and N-oxides thereof:

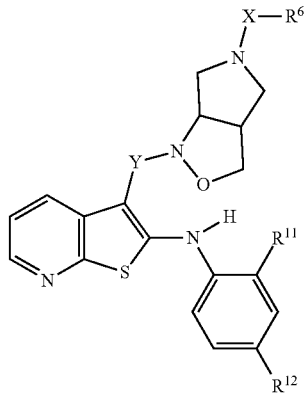

(IID)

wherein
Y, X, $R^6$, $R^{11}$ and $R^{12}$ are as defined above.

Specific novel compounds in accordance with the present invention include each of the compounds whose preparation is described in the accompanying Examples, and pharmaceutically acceptable salts and solvates thereof.

The present invention also provides a pharmaceutical composition which comprises a compound of formula (I) as defined above, or a pharmaceutically acceptable salt, solvate or N-oxide thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula $H—R^3$ with a compound of formula (III):

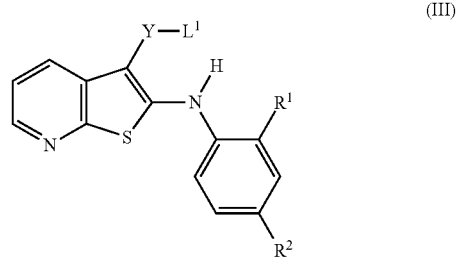

(III)

wherein Y, $R^1$ and $R^2$ are as defined above, and $L^1$ represents a suitable leaving group.

Where Y represents a linkage of formula C(O) the leaving group $L^1$ is typically a halogen atom, e.g. fluoro. Where Y represents a linkage of formula $S(O)_2$ the leaving group $L^1$ is typically a sulfonyl ester moiety, e.g. pentafluorophenoxy.

The reaction is conveniently effected in a suitable solvent, e.g. dichloromethane, typically under basic conditions, e.g. in the presence of an organic base such as N,N-diisopropylethylamine.

The intermediates of formula (III) wherein Y represents a linkage of formula C(O) and $L^1$ represents fluoro may suitably be prepared by reacting a compound of formula (IV):

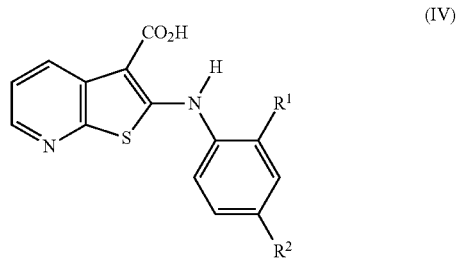

(IV)

wherein $R^1$ and $R^2$ are as defined above; with diethylaminosulfur trifluoride (DAST).

The reaction is conveniently effected in a suitable solvent, e.g. dichloromethane.

The intermediates of formula (IV) above may suitably be prepared by reacting a compound of formula (V) with a compound of formula (VI):

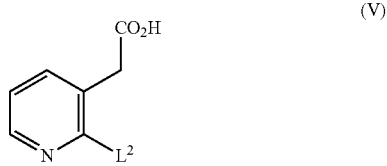

(V)

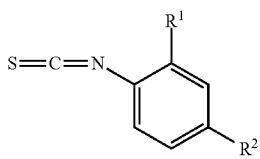

(VI)

wherein R¹ and R² are as defined above, and L² represents a suitable leaving group.

The leaving group L² is typically a halogen atom, e.g. chloro.

The reaction is conveniently effected, at an elevated temperature if necessary, in a suitable solvent, e.g. tetrahydrofuran, typically under basic conditions, e.g. in the presence of lithium diisopropylamide.

The intermediates of formula (VI) above may be prepared by the procedure described in WO 2007/088345.

The intermediates of formula (III) wherein Y represents a linkage of formula $S(O)_2$ and L¹ represents pentafluorophenoxy may suitably be prepared by reacting a compound of formula (VII):

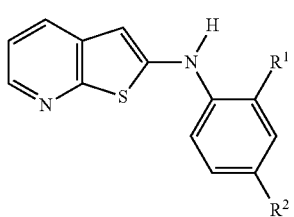

(VII)

wherein R¹ and R² are as defined above; with chlorosulfonic acid; followed by treatment with pentafluorophenol, typically in the presence of an organic base such as pyridine.

The intermediates of formula (VII) may suitably be prepared by decarboxylating a compound of formula (IV) as defined above. Decarboxylation is conveniently effected by heating compound (IV), typically at the reflux temperature, in an inert organic solvent, e.g. a hydrocarbon solvent such as toluene.

Where they are not commercially available, the starting materials of formula (V) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) wherein $R^3$ contains a nitrogen atom to which a tert-butoxycarbonyl (BOC) group is attached may be converted into the corresponding compound wherein $R^3$ contains an N—H functionality by treatment with an acid, e.g. a mineral acid such as hydrochloric acid, or an organic acid such as trifluoroacetic acid. Furthermore, the pyridine-N-oxide derivative of a compound of formula (I) may be converted into the corresponding compound of formula (I) by treatment with triphenyl phosphine and phosphorus trichloride.

A compound of formula (I) wherein $R^4$ or $R^5$ represents $C_{2-6}$ alkoxycarbonyl, e.g. methoxycarbonyl, may be converted into the corresponding compound wherein $R^4$ or $R^5$ represents carboxy by treatment with a base, e.g. an inorganic base such as sodium hydroxide.

A compound of formula (I) wherein $R^4$ or $R^5$ represents $C_{2-6}$ alkoxycarbonyl, e.g. methoxycarbonyl, may be converted into the corresponding compound wherein $R^4$ or $R^5$ represents hydroxymethyl by treatment with a reducing agent such as lithium borohydride.

A compound of formula (I) wherein $R^4$ or $R^5$ represents azido (—$N_3$) may be converted into the corresponding compound wherein $R^4$ or $R^5$ represents amino (—$NH_2$) by treatment with triphenylphosphine.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at any convenient subsequent stage utilising methods known from the art.

The following Examples illustrate the preparation of compounds according to the invention.

The compounds in accordance with this invention potently inhibit the activity of human MEK enzyme.

In Vitro MEK Assay

MEK1 activity was measured in a cascade assay initiated by active Raf, via activation of MEK, Erk2 and subsequent phosphorylation of fluorescein-labelled Erk-tide substrate in an assay based on fluorescence polarisation (IMAP). The assay was carried out in 20 mM Tris+5 mM $MgCl_2$+2 mM DL-dithiothreitol+0.01% Tween 20 pH 7.2, containing 1.5 nM unactive MEK, 100 nM unactive Erk and 200 nM Erk-tide (all concentrations are final concentrations). Compounds, or DMSO controls, were tested at a final concentration of 2%

DMSO, and the assay initiated in the presence of 5 μM ATP by addition of 1.25 nM active Raf in assay buffer. After 20 min at r.t., stop solution was added followed by IMAP binding beads, the assay mixture was then incubated for 90 min at r.t. (with shaking) and then read on a Molecular Devices LJL HT reader.

When tested in the above assay, the compounds of the accompanying Examples were all found to inhibit human MEK enzyme with $IC_{50}$ values of 10 μM or better.

EXAMPLES

Abbreviations

| | |
|---|---|
| DMSO | dimethylsulphoxide |
| DCM | dichloromethane |
| EtOAc | ethyl acetate |
| DMF | N,N-dimethylformamide |
| TFA | trifluoroacetic acid |
| $Ph_3P$ | triphenylphosphine |
| h | hour(s) |
| r.t. | room temperature |
| sat. | saturated |
| RT | retention time |
| br | broad |
| THF | tetrahydrofuran |
| EtOH | ethanol |
| DAST | diethylaminosulfur trifluoride |
| DIPEA | N,N-diisopropylethylamine |
| MeOH | methanol |
| $SiO_2$ | silica |
| min | minute(s) |
| aq | aqueous |
| conc. | concentrated |
| ES | electrospray |

All NMR spectra were obtained either at 300 MHz or 400 MHz.

Compounds were named with the aid of ACD Labs Name (v. 7.0) supplied by Advanced Chemical Development, Toronto, Canada.

Standard LCMS Method

The LC-MS system used comprises a Waters Alliance 2795 HT quaternary HPLC, Waters 996 Photo Diode Array (PDA) detector and Waters ZQ 4000 single quadrupole mass spectrometer. The ZQ can acquire data simultaneously in positive and negative electrospray ionisation modes.

ZQ Mass Spectrometer

| | | | |
|---|---|---|---|
| Capillary | 3.5 kV | Cone | 50 V |
| Extractor | 2 V | Source Temp | 80° C. |
| Desolvation Temp | 200° C. | Cone Gas | 150 L/h |
| Desolvation Gas | 250 L/h | Multiplier | 650 V |

Data were acquired in a full scan from 100 to 1000 m/z.

| | |
|---|---|
| Scan duration | 0.80 s |
| Interscan delay | 0.20 s |

HPLC

Analytical reverse phase separation was carried out on a Gemini C18 from Phenomenex 50×4.6 mm with 5 μm silica.

| | |
|---|---|
| Injection Volume | 5 μL |
| UV data | 240 to 400 nm |
| Sample Temperature | 20° C. |
| Column Temperature | 30° C. |
| Flow Rate | 0.9 mL/min |
| Split to ZQ | ~0.40 mL/min |

Solvent A: 90% 10 mM $NH_4HCO_2$ in water/0.1% formic acid/10% $CH_3CN$
Solvent B: 90% $CH_3CN$/0.1% formic acid/10% 10 mM $NH_4HCO_2$ in water
Solvent C: 90% 10 mM $NH_4HCO_2$ in water/0.1% ammonia/10% $CH_3CN$
Solvent D: 90% $CH_3CN$/10% 10 mM $NH_4HCO_2$ in water/0.1% ammonia
Gradient Program
For method 5_95_pH=3

| Time (min) | A % | B % | Flow | Curve |
|---|---|---|---|---|
| 0.00 | 95.0 | 5.0 | 0.900 | 1 |
| 2.00 | 5.0 | 95.0 | 0.900 | 6 |
| 4.00 | 5.0 | 95.0 | 0.900 | 6 |
| 5.00 | 95.0 | 5.0 | 0.900 | 6 |

For method 5_95_pH=10

| Time (min) | A % | B % | Flow | Curve |
|---|---|---|---|---|
| 0.00 | 95.0 | 5.0 | 0.900 | 1 |
| 2.00 | 5.0 | 95.0 | 0.900 | 6 |
| 4.00 | 5.0 | 95.0 | 0.900 | 6 |
| 5.00 | 95.0 | 5.0 | 0.900 | 6 |

Preparative UV-HPLC

The LC system comprises a Waters 2525 quaternary pump, a Waters 996 Photo Diode Array (PDA) detector, a Waters 2700 sample manager, a Column Fluidics Organiser and a Waters Fraction Collector operating in reverse phase at one of two pH systems.

Low pH System (Approximately pH 3.2)

The reverse phase separation was carried out on a Luna C18 from Phenomenex 100×21.2 mm with 5 μm silica.

| | |
|---|---|
| Injection Volume | 500 μL |
| UV data | 254 nm |
| Flow Rate | 20 mL/min |

Solvent A 90% water/10% $CH_3CN$/0.1% formic acid
Solvent B 90% $CH_3CN$/10% water/0.1% formic acid
High pH System (Approximately pH 9.5)

The reverse phase separation was carried out on a Gemini C18 from Phenomenex 150×21.2 mm with 10 μm silica.

| | |
|---|---|
| Injection Volume | 500 μL |
| UV data | 254 nm |
| Flow Rate | 20 mL/min |

Solvent C 90% 10 mM $NH_4HCO_2$ in water/0.1% ammonia/10% $CH_3CN$

Solvent D 90% CH$_3$CN/10% 10 mM NH$_4$HCO$_2$ in water/ 0.1% ammonia

Typical gradient profiles are described below:

Gradient Program for Low pH Method

| Time  | A %  | B %  | C % | D % | Flow | Curve |
|-------|------|------|-----|-----|------|-------|
| 0.00  | 95.0 | 5.0  | 0.0 | 0.0 | 20   | 1     |
| 9.00  | 5.0  | 95.0 | 0.0 | 0.0 | 20   | 6     |
| 11.00 | 5.0  | 95.0 | 0.0 | 0.0 | 20   | 6     |
| 11.50 | 95.0 | 5.0  | 0.0 | 0.0 | 20   | 6     |
| 12.00 | 95.0 | 5.0  | 0.0 | 0.0 | 20   | 6     |

Gradient Program for High pH Method

| Time  | A % | B % | C %  | D %  | Flow | Curve |
|-------|-----|-----|------|------|------|-------|
| 0.00  | 0.0 | 0.0 | 95.0 | 5.0  | 20   | 1     |
| 9.00  | 0.0 | 0.0 | 5.0  | 95.0 | 20   | 6     |
| 11.00 | 0.0 | 0.0 | 5.0  | 95.0 | 20   | 6     |
| 11.50 | 0.0 | 0.0 | 95.0 | 5.0  | 20   | 6     |
| 12.00 | 0.0 | 0.0 | 95.0 | 5.0  | 20   | 6     |

Intermediate 1

2-Chloro-3-(chloromethyl)pyridine

To a 500 mL, round-bottom, 3-necked flask equipped with dropping funnel and magnetic stirrer and set for reflux was prepared a solution of 2-chloro-3-(hydroxymethyl)-pyridine (25.0 g, 174 mmol) in DCM (250 mL) under positive nitrogen atmosphere. The solution was cooled to 10° C. and thionyl chloride (31.0 g) was added dropwise over 25 minutes (exothermic). The reaction was then heated to reflux for 90 minutes, at which point the reaction was deemed complete by HPLC. The reaction mixture was cooled below boiling point and the equipment set for distillation. A total of 110 mL of DCM was initially removed and replenished with fresh DCM (110 mL), followed by another 80 mL of DCM before cooling the solution to 5-10° C. The acidic mixture was treated with a saturated solution of sodium bicarbonate (3 volumes) to pH 10. The lower organic phase was separated and the aqueous phase extracted with DCM (2 volumes). The organic phases were gathered, dried on sodium sulfate, filtered and concentrated in vacuo to afford the title compound as a pale yellow oil in excellent purity and yield (24.8 g, 88%). $\delta_H$ (d$_6$-DMSO, 300 MHz) 8.45 (1H, dd), 8.10 (1H, dd), 7.50 (1H, dd), 4.85 (2H, s). LCMS (ES)$^+$ RT 3.00 min, m/e 162.1.

Intermediate 2

(2-Chloropyridin-3-yl)acetonitrile

In a 3 L reactor, set for reflux under positive nitrogen pressure and using a bleach scrubber, was prepared a solution of potassium cyanide (68.32 g, 1.04M) in EtOH (136 mL) and water (255 mL). The mixture was heated to reflux, at which point a solution of 2-chloro-3-(chloromethyl)pyridine (Intermediate 1; 170.0 g, 1.04M) in EtOH (170 mL) was added dropwise over 30 minutes. The whole mixture was maintained at reflux for a further 150 minutes. The mixture was then allowed to cool just below boiling point and the equipment set for distillation. A total of 8.5 volumes of EtOH were removed. On cooling, half a volume of water was added. At a temperature of 40° C., the solution was seeded and crystallised instantaneously. The thick beige slurry was allowed to cool to ambient temperature and then to 0° C. This mixture was filtered, rinsed with cold water (2 vols) and dried at 45° C. in a vacuum oven overnight. The title compound was afforded as a beige solid in excellent yield and purity (126.9 g, 80%). $\delta_H$ (d$_6$-DMSO, 300 MHz) 8.45 (1H, dd), 8.00 (1H, dd), 7.50 (1H, dd), 4.15 (2H, s). LCMS (ES)$^+$ RT 2.15 min, m/e 153.01 & 155.01 (M+1 & M+3, Product).

Intermediate 3

(2-Chloropyridin-3-yl)acetic acid

To a 2 L reactor, set for reflux, was stirred a pre-prepared 15% w/w solution of sodium hydroxide (5 vols) to which was added (2-chloropyridin-3-yl)acetonitrile (Intermediate 2; 276.4 g, 1.81M). The beige suspension was heated to reflux for 30 minutes, at which point the reaction was deemed complete by HPLC. The brown solution was then cooled to 0-5° C. and acidified to pH 1 with conc. HCl while keeping the temperature below 10° C., using concentrated hydrochloric acid (1.8 vols). An off-white solid precipitated and was left to mature for another hour before filtration. Once dried, the material was recrystallised from propan-2-ol (4 vols) to afford the title compound as an off-white material in excellent yield and purity (280.3 g, 90%). $\delta_H$ (d$_6$-DMSO, 300 MHz) 12.70 (1H, s), 8.35 (1H, dd), 7.85 (1H, dd), 7.40 (1H, dd), 4.25 (2H, s). LCMS (ES)$^+$ RT 1.75 min, m/e 171.99 (M+1, Product).

Intermediate 4

2-[(2-Fluoro-4-iodophenyl)amino]thieno[2,3-b]pyridine-3-carboxylic acid

To a stirred solution of diisopropylamine (35.3 mL, 250 mmol) in anhydrous THF (200 mL) cooled to −15° C. was added n-butyllithium (100 mL, 2.5M in hexanes, 250 mmol) slowly such that an internal temperature of between −10 and 0° C. was maintained. The resultant mixture was stirred at room temperature for 15 minutes before being cooled to 0° C. The solution of lithium diisopropylamide was added via cannula to a rapidly stirred suspension of (2-chloropyridin-3-yl) acetic acid (Intermediate 3; 21.4 g, 125 mmol) in anhydrous THF (400 mL) at 0° C. The temperature of the reaction mixture was maintained at 0° C. over the course of the addition. Upon complete addition of the lithium diisopropylamide solution the resultant bright yellow suspension was stirred at 0° C. for 15 minutes. A solution of 2-fluoro-4-iodo-1-isothiocyanaobenzene (WO 2007/088345) (34.9 g, 125 mmol) in anhydrous THF (200 mL) was then added to the reaction mixture via cannula and the mixture heated to 65° C. for 18 hours. The reaction mixture was cooled and the volatiles removed in vacuo. The resultant brown gum was redissolved in THF (200 mL), cooled to 0° C. and 10% aqueous acetic acid (500 mL) added slowly. Acetonitrile (~200 mL) was added slowly until a brown solid developed; the solid was isolated by filtration and washed with successive portions of diethyl ether and acetonitrile to give the title compound as a yellow crystalline solid (11.0 g, 21%). $\delta_H$ (DMSO-d$_6$) 8.42 (1H, d, J 6.7 Hz), 8.22 (1H, m), 7.73 (1H, m), 7.61 (1H, m), 7.46 (1H, t, J 8.6 Hz), 7.35-7.31 (1H, m). Exchangeable protons were not observed. LCMS (pH 10) RT 1.82 minutes, ES$^+$ 415 (M+H)$^+$, ES$^-$ 413 (M−H)$^-$.

Intermediate 5

2-[(2-Fluoro-4-iodophenyl)amino]thieno[2,3-b]pyridine-3-carbonyl fluoride

Intermediate 4 (7.80 g, 18.7 mmol) was suspended in dichloromethane (200 mL). DAST (2.80 mL, 20.8 mmol) was added and the mixture was stirred at room temperature for 3 hours. Ice cold water (3 mL) was added and stirring was continued for 5 minutes. Sodium sulfate (~25 g) was then added to absorb the water and dry solvent. After filtration, the filtrate was passed through a 70 g pre-packed silica column and eluted with dichloromethane (1 L). All the eluent was collected and concentrated in vacuo to give the title compound as a pale yellow solid (4.80 g, 61%). $\delta_H$ (DMSO-$d_6$) 10.03 (1H, br s), 8.33 (1H, dd, J 1.4, 4.7 Hz), 8.09 (1H, d, J 8.1 Hz), 7.91 (1H, dd, J 1.8, 9.7 Hz), 7.73 (1H, dd, J 1.0, 8.3 Hz), 7.49-7.42 (2H, m).

Intermediate 6

N-(2-Fluoro-4-iodophenyl)thieno[2,3-b]pyridin-2-amine

A suspension of Intermediate 4 (3 g, 7.2 mmol) in toluene (50 mL) was heated at reflux for 18 h. After this time the solvent was removed in vacuo to afford the title compound as a pale brown solid (2.7 g, quant). $\delta_H$ (CDCl$_3$) 8.42 (1H, dd, J 1.6, 4.7 Hz), 7.82 (1H, dd, J 1.4, 8.1 Hz), 7.46 (2H, m), 7.27-7.18 (2H, m), 6.77 (1H, s), 6.25 (1H, s). LCMS (pH 10) RT 3.36 minutes, (ES$^+$) 371 (M+H)$^+$.

Intermediate 7

Pentafluorophenyl 2-[(2-fluoro-4-iodophenyl)amino]thieno[2,3-b]pyridine-3-sulfonate A solution of Intermediate 6 (270 mg, 0.73 mmol) in DCM (25 mL) was cooled (acetone/CO$_2$ bath) before chlorosulfonic acid (0.24 ml, 3.65 mmol) was added dropwise. The mixture was placed in an ice bath and stirred for 5 h, before pyridine (1.2 mL, 14.6 mmol) and then pentafluorophenol (300 mg, 1.6 mmol) were added. After 18 h the reaction mixture was partitioned between DCM (100 mL) and water (100 mL). The organic layer was dried (Na$_2$SO$_4$) and concentrated in vacuo and after chromatography (SiO$_2$; DCM) gave the title compound as a white crystalline solid (395 mg, 88%). $\delta_H$ (CDCl$_3$) 8.57 (1H, s), 8.43 (1H, m), 8.15 (1H, m), 7.62 (2H, m), 7.39-7.27 (2H, m). LCMS (pH 3) RT 3.93 minutes, (ES$^+$) 617 (M+H)$^+$.

Intermediate 8

2-[(R)-4-(Methanesulfonyloxy)isoxazolidine-2-carbonyl]benzoic acid methyl ester 2-[(R)-4-Hydroxyisoxazolidine-2-carbonyl]benzoic acid methyl ester (prepared by the method of Martin et al., *Tetrahedron Lett.*, 2007, 47, 7635) (3.50 g, 14.0 mmol) was dissolved in dichloromethane (100 mL) and N,N-diisopropylethylamine (3.55 mL, 20.3 mmol), then methanesulfonyl chloride (1.40 mL, 18.5 mmol) was added and the mixture was stirred at room temperature for 18 hours. The mixture was washed with 0.1M HCl solution (100 mL), dried (Na$_2$SO$_4$) and concentrated in vacuo to give the title compound as a yellow oil (5.00 g, 100%). $\delta_H$ (DMSO-$d_6$) 7.92-7.46 (4H, m), 4.28 (1H, m) 4.17-4.14 (2H, m), 4.06-3.92 (2H, m), 3.82 (3H, s), 3.31 (3H, s). LCMS (ES$^+$) RT 1.45 minutes, 330 (M+H)$^+$ (pH 3).

Intermediate 9

(S)-4-Azidoisoxazolidine

Intermediate 8 (5.0 g, 14.0 mmol) was dissolved in dry DMF (25 mL) and sodium azide (1.04 g, 16.0 mmol) was added. The mixture was heated to 70° C. for 4 hours then 80° C. for a further 3 hours. After concentration in vacuo, chromatography (silica; ethyl acetate) gave an intermediate as a colourless oil (1.80 g, 43%). This intermediate was dissolved in 4M HCl (30 mL) and heated to reflux for 4 hours. After cooling in an ice bath the solid by-product was removed by filtration, washing with a little ice water (5 mL). The remaining aqueous fraction was freeze-dried to afford the title compound as an off-white solid (1.0 g, 45%). $\delta_H$(DMSO-$d_6$) 4.96 (1H, m), 4.24 (1H, dd, J 1.5, 9.6 Hz), 4.10 (1H, dd, J 4.4, 9.6 Hz), 3.66 (1H, dd, J 6.0, 12.0 Hz), 3.48 (1H, dd, J 1.5, 12.0 Hz).

Intermediate 10

[(S)-4-Azidoisoxazolidin-2-yl][2-(2-fluoro-4-iodophenylamino)thieno[2,3-b]pyridin-3-yl]methanone Intermediate 9 (700 mg, 4.65 mmol) was suspended in dichloromethane (50 mL) and DIPEA (2.40 mL, 14.0 mmol) was added. The mixture was stirred at room temperature until dissolution occurred. Intermediate 5 (1.93 g, 4.65 mmol) was added and the mixture was stirred at room temperature for 4 hours. After diluting with dichloromethane (100 mL) the mixture was washed with 0.05M HCl (200 mL), dried (Na$_2$SO$_4$) and concentrated in vacuo. Purification by chromatography (silica; 5% ethyl acetate, 95% dichloromethane) gave the title compound as a pale pink solid (1.35 g, 57%). $\delta_H$ (DMSO-$d_6$) 9.58 (1H, s, NH), 8.32 (1H, dd, J 1.6, 4.7 Hz), 7.95 (1H, dd, J 1.6, 8.1 Hz), 7.76 (1H, dd, J 1.9, 10.3 Hz), 7.59 (1H, m), 7.41-7.33 (2H, m), 4.78 (1H, m), 4.10 (1H, dd, J 6.4, 12.0 Hz), 4.03-3.98 (2H, m), 3.72 (1H, dd, J 1.8, 12.0 Hz). LCMS (ES$^+$) RT 1.52 minutes, 511 (M+H)$^+$ (pH 3).

Intermediate 11

5-Methylisoxazolidine-5-carboxylic acid methyl ester

Sodium hydroxide (5.75 g, 144 mmol) was dissolved in water (30 mL) and methanol (15 mL), then cooled to 10° C., followed by portionwise addition of hydroxylamine hydrochloride (10.0 g, 144 mmol), cooling in an ice bath to keep the temperature below 30° C. Formaldehyde solution (10.9 mL of a 37% aqueous solution, 144 mmol) was then added over 2 minutes. The mixture was stirred whilst methyl methacrylate (15.4 mL, 144 mmol) was added. The mixture was then heated to 70° C. for 4 hours before concentrating in vacuo. Distillation (using Kugelrohr at 0.2 ton, 100° C.) gave the title compound as a colourless oil (3.10 g, 15%). $\delta_H$ (CDCl$_3$) 6.00 (1H, br s), 3.76 (3H, s), 3.39-3.13 (2H, m), 2.56-2.46 (1H, m), 2.16-2.08 (1H, m), 1.54 (3H, s).

Example 1

2-({2-[(2-Fluoro-4-iodophenyl)amino]thieno[2,3-b]pyridin-3-yl}carbonyl)isoxazolidin-4-ol Intermediate 5 (250 mg, 0.60 mmol) was dissolved in dry dichloromethane (20 mL) and isoxazolidin-4-ol hydrochloride (251 mg, 1.20 mmol) and N,N-diisopropyl-ethylamine (310 µL, 1.80 mmol) were added. The mixture was stirred at ambient temperature for 18 h. The mixture was then diluted with dichloromethane (200 mL), then washed with water (50 mL) and saturated aqueous brine solution (50 mL). The organics were dried (Na$_2$SO$_4$) and concentrated in vacuo. The residual solids were recrystallised from ethyl acetate (30 mL) to give the title compound as a white solid (110 mg, 38%). $\delta_H$ (DMSO-d$_6$) 9.52 (1H, br s), 8.34 (1H, dd, J 4.6, 1.5 Hz), 7.95 (1H, dd, J 8.1, 1.5 Hz), 7.75 (1H, dd, J 10.4, 1.8 Hz), 7.58 (1H, d, J 9.1 Hz), 7.41-7.32 (2H, m), 5.45 (1H, d, J 3.8 Hz), 4.67 (1H, m), 3.95-3.89 (2H, m), 3.84-3.80 (1H, m), 3.54 (1H, d, J 11.4 Hz). LCMS (ES$^+$) RT 2.55 minutes, method pH 3, 486 (M+H)$^+$.

Example 2

(4R)-2-({2-[(2-Fluoro-4-iodophenyl)amino]thieno[2,3-b]pyridin-3-yl}carbonyl)-isoxazolidin-4-ol Intermediate 5 (1.00 g, 2.40 mmol) was dissolved in dry dichloromethane (50 mL) and (4R)-isoxazolidin-4-ol hydrochloride (prepared by the method of Martin et al., *Tetrahedron Lett.*, 2007, 47, 7635) (1.00 g, 1.20 mmol) and N,N-diisopropylethylamine (1.24 mL, 7.20 mmol) were added. The mixture was stirred at room temperature for 4 h. Water (100 mL) was added and the mixture concentrated in vacuo to remove the organics. The resultant solid was isolated by filtration and dried under suction. The crude material was resuspended in ethyl acetate (15 mL) and slurried for 5 minutes before filtering and drying under vacuum to give the title compound as a white solid (1.0 g, 86%). $\delta_H$ (DMSO-d$_6$) 9.52 (1H, br s), 8.34 (1H, dd, J 4.6, 1.5 Hz), 7.95 (1H, dd, J 8.1, 1.5 Hz), 7.75 (1H, dd, J 10.4, 1.8 Hz), 7.58 (1H, d, J 9.1 Hz), 7.41-7.32 (2H, m), 5.45 (1H, d, J 3.8 Hz), 4.67 (1H, m), 3.95-3.89 (2H, m), 3.84-3.80 (1H, m), 3.54 (1H, d, J 11.4 Hz). LCMS (ES$^+$) RT 2.55 minutes, method pH 3, 486 (M+H)$^+$.

Example 3

(4S)-2-({2-[(2-Fluoro-4-iodophenyl)amino]thieno[2,3-b]pyridin-3-yl}carbonyl)-isoxazolidin-4-ol Intermediate 5 (300 mg, 0.72 mmol) was dissolved in dry dichloromethane (10 mL) and (4S)-isoxazolidin-4-ol hydrochloride (prepared by the method of Martin et al., *Tetrahedron Lett.*, 2007, 47, 7635) (180 mg, 1.44 mmol) and N,N-diisopropylethylamine (0.37 mL, 2.16 mmol) were added. The mixture was stirred at room temperature for 4 h. Water (20 mL) was added and the mixture concentrated in vacuo to remove the organics. The resultant solid was isolated by filtration and dried under suction. The crude material was resuspended in ethyl acetate (15 mL) and slurried for 5 minutes before filtering and drying under vacuum to give the title compound as a white solid (200 mg, 57%). $\delta_H$ (DMSO-d$_6$) 9.52 (1H, br s), 8.34 (1H, dd, J 4.6, 1.5 Hz), 7.95 (1H, dd, J 8.1, 1.5 Hz), 7.75 (1H, dd, J 10.4, 1.8 Hz), 7.58 (1H, d, J 9.1 Hz), 7.41-7.32 (2H, m), 5.45 (1H, d, J 3.8 Hz), 4.67 (1H, m), 3.95-3.89 (2H, m), 3.84-3.80 (1H, m), 3.54 (1H, d, J 11.4 Hz). LCMS (ES$^+$) RT 2.55 minutes, method pH 3, 486 (M+H)$^+$.

Example 4

2-({2-[(2-Fluoro-4-iodophenyl)amino]thieno[2,3-b]pyridin-3-yl}sulfonyl)isoxazolidin-4-ol Intermediate 7 (200 mg, 0.32 mmol) was dissolved in dichloromethane (10 mL) and N,N-diisopropylethylamine (110 µl 0.64 mmol) and isoxazolidin-4-ol hydrochloride (Key Organics, UK) (41 mg, 0.32 mmol) were added. The reaction mixture was stirred at r.t. under nitrogen for 18 h. Dichloromethane (20 mL) was added and the solution washed with water (10 mL), dried (Na$_2$SO$_4$), filtered and concentrated in vacuo. The residue was purified by chromatography (silica; 25% EtOAc, 75% CH$_2$Cl$_2$) to give the title compound as an off-white solid (60 mg, 36%). $\delta_H$ (DMSO-d$_6$) 9.22 (1H, br s), 8.34 (1H, d, J 4.6 Hz), 8.11 (1H, d, J 8.2 Hz), 7.88-7.85 (1H, m), 7.71-7.68 (1H, m), 7.47-7.41 (2H, m), 5.47 (1H, d, J 4.3 Hz), 4.69-4.65 (1H, m), 4.04-3.84 (2H, m), 3.69-3.66 (1H, m), 3.42-3.38 (1H, m). LCMS (pH 3) RT 2.81 minutes, (ES$^+$) 522 (M+H)$^+$.

Example 5

[(S)-4-Aminoisoxazolidin-2-yl][2-(2-fluoro-4-iodophenylamino)thieno[2,3-b]pyridin-3-yl]methanone Intermediate 10 (1.32 g, 2.59 mmol) was dissolved in THF (60 mL) and water (25 mL). Ph$_3$P (681 mg, 2.60 mmol) was added and the mixture stirred at r.t. for 18 hours. The mixture was concentrated in vacuo then purified by chromatography (silica; 5% methanol, 95% dichloromethane) to afford the title compound as a yellow solid (270 mg, 22%). $\delta_H$ (DMSO-d$_6$) 8.32 (1H, dd, J 1.6, 4.7 Hz), 7.93 (1H, dd, J 1.6, 8.1 Hz), 7.74 (1H, dd, J 1.9, 10.3 Hz), 7.57 (1H, m), 7.40-7.32 (2H, m), 4.52 (3H, br s), 3.96 (1H, m), 3.91-3.78 (2H, m), 3.63 (1H, m), 3.46 (1H, m). LCMS (ES$^+$) RT 1.73 minutes, 485 (M+H)$^+$ (pH 3).

Example 6

(4-Azidoisoxazolidin-2-yl)[2-(2-fluoro-4-iodophenylamino)thieno[2,3-b]pyridin-3-yl]-methanone The title compound was prepared in an analogous manner to the (S)-isomer (Intermediate 10). $\delta_H$ (DMSO-d$_6$) 9.58 (1H, s, NH), 8.32 (1H, dd, J 1.6, 4.7 Hz), 7.95 (1H, dd, J 1.6, 8.1 Hz), 7.76 (1H, dd, J 1.9, 10.3 Hz), 7.59 (1H, m), 7.41-7.33 (2H, m), 4.78 (1H, m), 4.10 (1H, dd, J 6.4, 12.0 Hz), 4.03-3.98 (2H, m), 3.72 (1H, dd, J 1.8, 12.0 Hz). LCMS (ES$^+$) RT 1.52 minutes, 511 (M+H)$^+$ (pH 3).

Example 7

(4-Aminoisoxazolidin-2-yl)[2-(2-fluoro-4-iodophenylamino)thieno[2,3-b]pyridin-3-yl]-methanone Example 6 (1.32 g, 2.59 mmol) was dissolved in THF (60 mL) and water (25 mL). Ph$_3$P (681 mg, 2.60 mmol) was added and the mixture was stirred at room temperature for 18 hours. The mixture was concentrated in vacuo then purified by chromatography (silica; 5% methanol, 95% dichloromethane) to afford the title compound as a yellow solid (270 mg, 22%). $\delta_H$ (DMSO-d$_6$) 8.32 (1H, dd, J 1.6, 4.7 Hz), 7.93 (1H, dd, J 1.6, 8.1 Hz), 7.74 (1H, dd, J 1.9, 10.3 Hz), 7.57 (1H, m), 7.40-7.32 (2H, m), 4.52 (3H, br s), 3.96 (1H, m), 3.91-3.78 (2H, m), 3.63 (1H, m), 3.46 (1H, m). LCMS (ES$^+$) RT 1.73 minutes, 485 (M+H)$^+$ (pH 3).

Example 8

2-[2-(2-Fluoro-4-iodophenylamino)thieno[2,3-b]pyridine-3-carbonyl]-5-methyl-isoxazolidine-5-carboxylic acid methyl ester Intermediate 5 (1.00 g, 2.40 mmol) and DIPEA (0.42 mL, 2.40 mmol) were dissolved in dichloromethane (30 mL) and Intermediate 11 (350 mg, 2.40 mmol) was added. The mixture was stirred at room temperature for 4 hours, concentrated in vacuo and purified by chromatography (silica; dichloromethane, then 10% ethyl acetate:90% dichloromethane). The title compound was isolated as a pale yellow solid (1.00 g, 77%). $\delta_H$ (DMSO-$d_6$) 9.38 (1H, s), 8.32 (1H, dd, J 1.6, 4.7 Hz), 7.97 (1H, dd, J 1.6, 8.2 Hz), 7.75 (1H, dd, J 1.9, 10.3 Hz), 7.58 (1H, m), 7.40-7.33 (2H, m), 4.06-3.97 (1H, m), 3.80-3.72 (1H, m), 3.50 (3H, s), 2.75-2.67 (1H, m), 2.30-2.20 (1H, m), 1.43 (3H, s). LCMS (ES$^+$) RT 3.23 minutes, 542 (M+H)$^+$ (pH 3).

Example 9

[2-(2-Fluoro-4-iodophenylamino)thieno[2,3-b]pyridin-3-yl][5-(hydroxymethyl)-5-methyl-isoxazolidin-2-yl]methanone Example 8 (350 mg, 0.65 mmol) was dissolved in dry THF (30 mL). Lithium borohydride (28 mg, 1.30 mmol) was added and the mixture was stirred at room temperature for 3 hours. The mixture was treated with water (80 mL) and acidified with acetic acid (1 mL). The resultant solid was filtered off and washed with water (20 mL) and dried under suction. LCMS showed MH+14, presumed to be a borane complex of the desired product. The solid was dissolved in methanol (25 mL) and stirred for 3 days to effect breakdown of the complex. The product was purified by reverse-phase HPLC to give the title compound, after freeze drying, as a pale yellow solid (38 mg, 10%). $\delta_H$ (DMSO-$d_6$) 8.31 (1H, m), 7.96 (1H, m), 7.73 (1H, m), 7.55 (1H, m), 7.38-7.29 (2H, m), 3.85-3.82 (2H, m), 3.45 (1H, br s), 3.31-3.28 (2H, m), 2.32-2.26 (1H, m), 2.00-1.93 (1H, m), 1.15 (3H, s). LCMS (ES$^+$) RT 2.69 minutes, 514 (M+H)$^+$ (pH 3).

Example 10

2-[2-(2-Fluoro-4-iodophenylamino)thieno[2,3-b]pyridine-3-carbonyl]-5-methyl-isoxazolidine-5-carboxylic acid Example 8 was dissolved in THF (20 mL) and NaOH solution (0.26 mL of a 10% aqueous solution, 0.65 mmol) was added. The mixture was stirred at room temperature for 4 hours. The volatiles were then removed in vacuo. The residue was treated with water (20 mL) and acidified with acetic acid (0.5 mL). After agitating for 1 minute the resultant solid was isolated by filtration, washed with water and dried under vacuum at 50° C. to give the title compound as an off-white solid (316 mg, 93%). $\delta_H$ (DMSO-$d_6$) 13.26 (1H, br s), 9.95 (1H, br s), 8.28 (1H, dd, J 1.6, 4.6 Hz), 7.98 (1H, dd, J 1.6, 8.1 Hz), 7.74 (1H, dd, J 1.9, 10.2 Hz), 7.58 (1H, m), 7.36-7.31 (2H, m), 3.89-3.77 (2H, m), 2.73-2.65 (1H, m), 2.27-2.15 (1H, m), 1.42 (3H, s). LCMS (ES$^+$) RT 2.63 minutes, 528 (M+H)$^+$ (pH 3).

Example 11

Benzyl 1-({2-[(2-fluoro-4-iodophenyl)amino]thieno[2,3-b]pyridin-3-yl}carbonyl)-tetrahydro-1H-pyrrolo[3,4-c]isoxazole-5(3H)-carboxylate To a stirred solution of benzyl tetrahydro-1H-pyrrolo[3,4-c]isoxazole-5(3H)-carboxylate (prepared by the procedure described by J. Ji et al. in *J. Med. Chem.*, 2007, 50, 5493-5508) (0.1492 g, 0.60 mmol) in DCM (10 mL) was added DIPEA (0.109 mL, 0.63 mmol) followed by Intermediate 5 (0.250 g, 0.60 mmol) and the solution was stirred at room temperature for 24 hours. Purification by column chromatography (SiO$_2$; 1:1 hexane/EtOAc) gave the title compound as a pale yellow glass (0.22 g, 57%). $\delta_H$ (DMSO-$d_6$) 9.51 (1H, s), 8.32 (1H, d, J 4.6 Hz), 7.87 (1H, d, J 8.1 Hz), 7.72 (1H, d, J 10.4 Hz), 7.56 (1H, d, J 8.6 Hz), 7.38-7.29 (7H, m), 5.09 (2H, s), 4.96 (1H, t), 3.95 (1H, d, J 8.3 Hz), 3.88 (1H, t, J 5.6, 8.2 Hz), 3.80-3.50 (3H, m), 3.41 (2H, d, J 7.6 Hz). LCMS (ES+) 645.1 (M+H)$^+$, RT 3.8 minutes (pH 3).

Example 12

{2-[(2-Fluoro-4-iodophenyl)amino]thieno[2,3-b]pyridin-3-yl}(hexahydro-1H-pyrrolo[3,4-c]isoxazol-1-yl)methanone Example 11 (0.2 g, 0.3 mmol) was stirred in TFA (5 mL) and heated at 50° C. for 24 hours. The reaction mixture was diluted with DCM and the volatiles were removed in vacuo to afford an orange gum. The crude material was dissolved in DCM and washed with saturated aqueous sodium bicarbonate solution. The combined organic phases were dried by passage through a phase separator cartridge and concentrated under vacuum to give a yellow solid. Purification by column chromatography (SiO$_2$; 10:1 DCM/MeOH) gave the title compound as a pale yellow glass (0.075 g, 47%). The product was freeze-dried to give a pale yellow solid. $\delta_H$ (DMSO-$d_6$) 8.32 (1H, dd, J 1.5, 3.1 Hz), 7.94 (1H, dd, J 1.5, 6.6 Hz), 7.75 (1H, dd, J 1.9, 8.5 Hz), 7.58 (1H, d, J 9.4 Hz), 7.39-7.31 (2H, m), 4.77 (1H, m), 3.91-3.84 (2H, m), 3.20 (1H, m), 3.04 (1H, dd, J 6.0, 5.9 Hz), 2.98 (2H, m), 2.85 (1H, dd, J 3.9, 3.9 Hz). LCMS (ES+) 511 (M+H)$^+$, RT 2.06 minutes (pH 3).

What is claimed:
1. A compound of formula (I), or a pharmaceutically acceptable salt or N-oxide thereof:

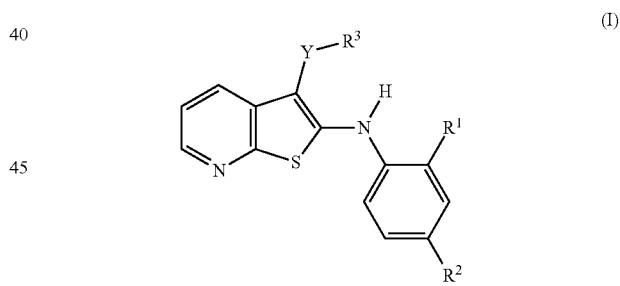

wherein
Y is C(O) or S(O)$_2$;
R$^1$ is hydrogen, halogen, cyano, nitro, C$_{1-6}$ alkyl, trifluoromethyl, C$_{1-6}$ alkoxy, trifluoromethoxy, C$_{1-6}$ alkylthio, C$_{1-6}$ alkylsulphinyl or C$_{1-6}$ alkylsulphonyl;
R$^2$ is halogen, nitro, cyano, C$_{1-6}$ alkyl, C$_{2-6}$ alkynyl, hydroxy(C$_{1-6}$)alkyl or formyl; and
R$^3$ is selected from the group consisting of formulas (b) and (e):

-continued

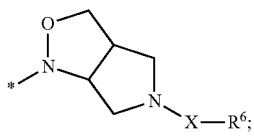

(e)

wherein the asterisk (*) identifies the point of attachment of $R^3$ to the remainder of the compound of formula I;

$R^4$ and $R^5$ are each independently hydrogen, $C_{1-6}$ alkyl, $C_{1-6}$ alkoxy, $C_{1-6}$ alkylamino($C_{1-6}$)alkoxy, $C_{1-6}$ alkoxy($C_{1-6}$)alkyl, $C_{1-6}$ alkylthio, $C_{1-6}$ alkylsulphonyl, hydroxy, hydroxy($C_{1-6}$)alkyl, amino($C_{1-6}$)alkyl, nitro($C_{1-6}$)alkyl, cyano, trifluoromethyl, $C_{2-6}$ alkylcarbonyl, carboxy, $C_{2-6}$ alkoxycarbonyl, azido, amino, $C_{1-6}$ alkylamino, di($C_{1-6}$)alkylamino, bis[hydroxy($C_{1-6}$)alkyl]amino, $C_{1-6}$ alkylamino($C_{1-6}$)alkylamino, arylamino, heteroarylamino, $C_{2-6}$ alkylcarbonylamino, $C_{2-6}$ alkoxycarbonylamino, [($C_{2-6}$)alkoxycarbonyl][($C_{1-6}$)alkyl]amino, bis[($C_{2-6}$)alkoxycarbonyl($C_{1-6}$)alkyl]amino, $C_{2-6}$ alkoxycarbonylamino($C_{1-6}$)alkyl or aminocarbonyl;

X is a covalent bond, C(O), S(O)$_2$, C(O)O or C(O)N($R^7$);

$R^6$ is hydrogen or trifluoromethyl; or $C_{1-6}$ alkyl, $C_{3-7}$ cycloalkyl, $C_{3-7}$ cycloalkyl($C_{1-6}$) alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which is optionally substituted with one or more substituents selected from the group consisting of:

halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$) alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl and di($C_{1-6}$)-alkylaminosulphonyl; and $R^7$ is hydrogen or $C_{1-6}$ alkyl.

2. A compound according to claim 1 wherein $R^3$ is:

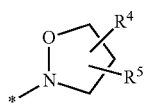

(b)

3. A compound according to claim 1 wherein $R^4$ and $R^5$ are each independently hydrogen, $C_{1-6}$ alkyl, hydroxy, hydroxy($C_{1-6}$)alkyl, carboxy, $C_{2-6}$ alkoxycarbonyl, azido or amino.

4. A compound according to claim 2 wherein $R^4$ and $R^5$ are each independently hydrogen, $C_{1-6}$ alkyl, hydroxy, hydroxy($C_{1-6}$)alkyl, carboxy, $C_{2-6}$ alkoxycarbonyl, azido or amino.

5. A compound or pharmaceutically acceptable salt or N-oxide thereof according to claim 1, having the following formula (IIA):

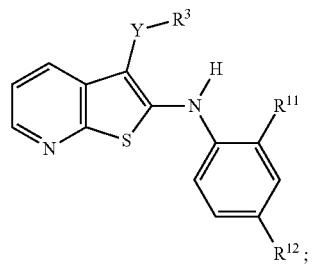

(IIA)

wherein $R^{11}$ is halogen; and $R^{12}$ is halogen, nitro, cyano, $C_{2-6}$ alkynyl, hydroxy($C_{1-6}$) alkyl or formyl.

6. A compound according to claim 5, wherein $R^{11}$ is fluoro or chloro.

7. A compound according to claim 5 wherein $R^{12}$ is iodo.

8. A compound or pharmaceutically acceptable salt or N-oxide thereof according to claim 5, having the following formula (IIB):

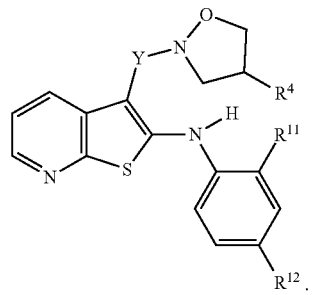

(IIB)

9. A compound according to claim 8, wherein $R^{11}$ is fluoro or chloro.

10. A compound according to claim 8 wherein $R^{12}$ is iodo.

11. A compound or pharmaceutically acceptable salt or N-oxide thereof according to claim 5, having the following formula (IIC):

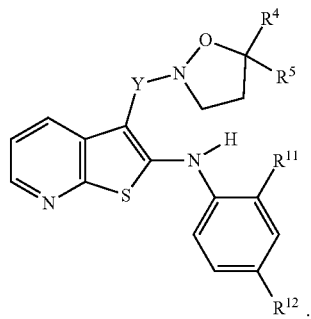

(IIC)

12. A compound according to claim 11, wherein $R^{11}$ is fluoro or chloro.

13. A compound according to claim 11 wherein $R^{12}$ is iodo.

14. A compound or pharmaceutically acceptable salt or N-oxide thereof according to claim 5, having the following formula (IID):

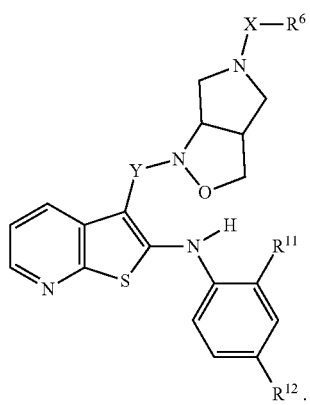

(IID)

15. A compound according to claim 14, wherein $R^{11}$ is fluoro or chloro.

16. A compound according to claim 14 wherein $R^{12}$ is iodo.

17. A compound or pharmaceutically acceptable salt or N-oxide thereof according to claim 1, which is selected from the group consisting of:

2-({2-[(2-Fluoro-4-iodophenyl)amino]thieno[2,3-b]pyridin-3-yl}carbonyl)-isoxazolidin-4-ol;

(4R)-2-({2-[(2-Fluoro-4-iodophenyl)amino]thieno[2,3-b]pyridin-3-yl}carbonyl)-isoxazolidin-4-ol;

(4S)-2-({2-[(2-Fluoro-4-iodophenyl)amino]thieno[2,3-b]pyridin-3-yl}carbonyl)-isoxazolidin-4-ol;

2-({2-[(2-Fluoro-4-iodophenyl)amino]thieno[2,3-b]pyridin-3-yl}sulfonyl)-isoxazolidin-4-ol;

[(S)-4-Aminoisoxazolidin-2-yl][2-(2-fluoro-4-iodophenylamino)thieno[2,3-b]pyridin-3-yl]methanone;

(4-Azidoisoxazolidin-2-yl)[2-(2-fluoro-4-iodophenylamino)thieno[2,3-b]pyridin-3-yl]-methanone;

(4-Aminoisoxazolidin-2-yl) [2-(2-fluoro-4-iodophenylamino)thieno[2,3-b]pyridin-3-yl]-methanone;

2-[2-(2-Fluoro-4-iodophenylamino)thieno[2,3-b]pyridine-3-carbonyl]-5-methyl-isoxazolidine-5-carboxylic acid methyl ester;

[2-(2-Fluoro-4-iodophenylamino)thieno[2,3-b]pyridin-3-yl][5-(hydroxymethyl)-5-methyl-isoxazolidin-2-yl)methanone;

2-[2-(2-Fluoro-4-iodophenylamino)thieno[2,3-b]pyridine-3-carbonyl]-5-methyl-isoxazolidine-5-carboxylic acid;

Benzyl 1-({2-[(2-fluoro-4-iodophenyl)amino]thieno[2,3-b]pyridin-3-yl}carbonyl)-tetrahydro-1H-pyrrolo[3,4-c]isoxazole-5(3H)-carboxylate; and {2-[(2-Fluoro-4-iodophenyl)amino]thieno[2,3-b]pyridin-3-yl}(hexahydro-1H-pyrrolo[3,4-c]isoxazol-1-yl)methanone.

18. A pharmaceutical composition comprising a compound or a pharmaceutically acceptable salt or N-oxide thereof according to claim 1, and a pharmaceutically acceptable carrier.

* * * * *